United States Patent
Leibig et al.

(10) Patent No.: US 12,322,507 B2
(45) Date of Patent: Jun. 3, 2025

(54) SYSTEM AND METHOD FOR IDENTIFYING BREAST CANCER

(71) Applicant: MX Healthcare GmbH, Berlin (DE)

(72) Inventors: Christian Leibig, Munich (DE); Stefan Bunk, Berlin (DE); Maximilian Brandstaetter, Berlin (DE)

(73) Assignee: MX Healthcare GmbH, Berlin (DE)

( * ) Notice: Subject to any disclaimer, the term of this patent is extended or adjusted under 35 U.S.C. 154(b) by 447 days.

(21) Appl. No.: 17/731,229

(22) Filed: Apr. 27, 2022

(65) Prior Publication Data

US 2023/0352172 A1    Nov. 2, 2023

(51) Int. Cl.
  *G16H 50/20*     (2018.01)
  *G06T 7/00*      (2017.01)
  *G16H 30/40*     (2018.01)

(52) U.S. Cl.
  CPC .......... *G16H 50/20* (2018.01); *G06T 7/0012* (2013.01); *G16H 30/40* (2018.01); *G06T 2207/20081* (2013.01); *G06T 2207/30068* (2013.01)

(58) Field of Classification Search
  CPC ...... G16H 50/20; G16H 30/40; G06T 7/0012; G06T 2207/20081; G06T 2207/30068
  USPC ...................... 382/128, 156, 159
  See application file for complete search history.

(56) References Cited

U.S. PATENT DOCUMENTS

| | | | | |
|---|---|---|---|---|
| 2002/0029157 | A1* | 3/2002 | Marchosky | G16H 40/67 705/3 |
| 2009/0264758 | A1* | 10/2009 | Fujita | A61B 8/483 600/443 |
| 2019/0082336 | A1* | 3/2019 | Wahlstrom | H04W 24/06 |
| 2020/0364587 | A1 | 11/2020 | Kapur et al. | |

(Continued)

FOREIGN PATENT DOCUMENTS

WO    WO-2022221712 A1 * 10/2022

OTHER PUBLICATIONS

Christian Leibig et al.; "Leveraging uncertainty information from deep neural networks for disease detection"; Scientific Reports; www.nature.com/scientificreports; published on-line Dec. 19, 2017; pp. 1-14.

(Continued)

*Primary Examiner* — Jamares Q Washington
(74) *Attorney, Agent, or Firm* — Gordon Rees Scully & Mansukhani, LLP (57) ABSTRACT

An exemplary embodiment of the present invention relates to a system for identifying breast cancer based on at least one image of a patient's breast, the system comprising: an evaluation unit configured to analyze the image, wherein the evaluation unit generates a diagnosis result that labels the image as confident if the confidence in the evaluation result exceeds a given confidence level, and otherwise generates a diagnosis result that labels the image as unconfident, a request unit configured to generate an evaluation-request signal that requests an additional external evaluation of the image, if the diagnosis result labels the image as unconfi- (Continued)

dent, and a transfer unit having an input port for receiving the result of the additional external evaluation, and an output port for outputting the diagnosis result of the evaluation unit, wherein the transfer unit is configured to block access to the diagnosis result of the evaluation unit until the result of the additional external evaluation has been received.

21 Claims, 8 Drawing Sheets

(56) References Cited

U.S. PATENT DOCUMENTS

| | | |
|---|---|---|
| 2021/0035680 A1 | 2/2021 | Chen et al. |
| 2021/0313043 A1 | 10/2021 | Kecskemethy et al. |
| 2022/0223293 A1* | 7/2022 | Steinberg-Koch ....... G06N 3/08 |

OTHER PUBLICATIONS

European Search Report dated Jul. 18, 2023 issued by the European Patent Office in related European Patent Application No. 23 166 969.8.

* cited by examiner

SYSTEM AND METHOD FOR IDENTIFYING BREAST CANCER

The invention relates to systems and methods for identifying breast cancer.

BACKGROUND OF THE INVENTION

Mammography is the most common screening test for breast cancer. Mammography is a process where low-energy X-rays are used to examine the human breast for diagnosis and screening. The goal of mammography is the early detection of breast cancer, typically through detection of characteristic masses or microcalcifications.

Artificial intelligence (AI) algorithms for interpreting mammograms have the potential to improve the effectiveness of population breast cancer screening programmes if they can detect cancers, including interval cancers, without contributing substantially to overdiagnosis, as discussed in the publication "Artificial intelligence (AI) to enhance breast cancer screening: protocol for population-based cohort study of cancer detection" (Marinovich M L, Wylie E, Lotter W, Pearce A, Carter S M, Lund H, Waddell A, Kim J G, Pereira G F, Lee C I, Zackrisson S, Brennan M, Houssami N. BMJ Open. 2022 Jan. 3; 12(1):e054005. doi: 10.1136/bmjopen-2021-054005. PMID: 34980622; PMCID: PMC8724814).

OBJECTIVE OF THE PRESENT INVENTION

An objective of the present invention is to provide a system and a method that allows breast cancer screening with minimal work-load for medical service personnel.

BRIEF SUMMARY OF THE INVENTION

An exemplary embodiment of the present invention relates to a system for identifying breast cancer based on at least one image of a patient's breast, the system comprising:
- an evaluation unit configured to analyze the image, wherein the evaluation unit generates a diagnosis result that labels the image as confident if the confidence in the evaluation result exceeds a given confidence level, and otherwise generates a diagnosis result that labels the image as unconfident,
- a request unit configured to generate an evaluation-request signal that requests an additional external evaluation of the image, if the diagnosis result labels the image as unconfident, and
- a transfer unit having an input port for receiving the result of the additional external evaluation, and an output port for outputting the diagnosis result of the evaluation unit,
- wherein the transfer unit is configured to block access to the diagnosis result of the evaluation unit until the result of the additional external evaluation has been received.

The above embodiment is capable of restricting the involvement of a third party (such as medical personnel (doctors) or other technical evaluation devices) to unconfident cases. Furthermore, in case of a detected unconfident case, the system makes sure that the diagnosis results of the evaluation unit will not influence the additional external evaluation by the third party. To this end, the transfer unit blocks access to the system's diagnosis results until the additional external evaluation has been carried out.

The confidence in the evaluation result may be regarded as sufficiently high, i.e. as exceeding said given confidence level, if—in case of a cancer diagnosis—the likelihood of cancer exceeds a given cancer-related threshold, and—in case of a no-cancer diagnosis—the likelihood of cancer is below a given no-cancer-related threshold. The cancer-related threshold and the no-cancer-related threshold may differ or may be identical.

The transfer unit is preferably configured to automatically output the diagnosis result of the evaluation unit at the output port upon receipt of the result of the additional external evaluation.

The evaluation unit may be configured to further evaluate a metadata vector that comprises cancer-risk-relevant data of the patient.

The further evaluation of the metadata vector may include generating the diagnosis result based on the metadata vector in order to generate a vector-based diagnosis result.

The evaluation unit is preferably configured to generate a medical report if the diagnosis result is labelled as confident.

The further evaluation of the metadata vector may also affect the medical report. For instance, the generation of the medical report may be based on the metadata vector in order to generate a vector-based medical report.

The evaluation unit preferably adds a recommendation regarding time of a next screening and/or the modality of the next screening, to the vector-based medical report based on the evaluation of the metadata vector.

The vector components of the metadata vector preferably specify one or more of the following criteria: the number of cancers in the patient's first degree family, the number of breast cancers in the patient's first degree family, the number of cancers in the patient's second degree family, the number of breast cancers in the patient's second degree family, the patient's age, time since prior cancer diagnosis, genetic information, mutations in the BRCA1 gene, mutations in the BRCA2 gene, existence and type of palpable lesions.

The evaluation unit may be configured to additionally evaluate one or more stored prior breast images of the same patient. Such prior breast images may have been taken during one or more evaluations prior to a current evaluation.

The additional evaluation of said one or more prior breast images may include comparing at least one stored prior breast image with at least one current breast image that is taken during said current evaluation. The result of such a comparison may be included in the generation of the diagnosis result.

The evaluation unit may be configured to add markings to the image. The markings may include surroundings (like circles, rectangles or the like) and/or changed colours (for instance highlighting) in unclear sections of the breast image. The term "unclear sections" refers to sections that could not be confidently identified as either cancer-free or cancer-affected.

The transfer unit preferably outputs the added markings upon receipt of the result of the additional external evaluation or upon receipt of an external support-request signal at the input port.

The evaluation unit preferably uses artificial intelligence for the analysis of the breast images. For instance, the evaluation unit may comprise a machine learned model (e.g. a neural network, a Gaussian process and/or a Bayesian model).

The system may store available results of external evaluations for use in later training sessions of the artificial intelligence.

Since the system requires the input of additional external evaluations, the system may also comprise an integrated training unit that is configured to train the artificial intelligence (e.g. the machine learned model).

The transfer unit preferably transfers the results of the additional external evaluations towards the training unit.

The training unit preferably generates training data on the basis of the results of the additional external evaluation and the corresponding images. Then, the training unit may train the artificial intelligence (e.g. the machine learned model) on the basis of the generated training data.

The system may generate a trigger signal in order to trigger a training session when the number of stored external evaluations exceeds a given number and/or the time that has passed since the last training session exceeds a given threshold.

The training unit may be configured to carry out an individual training session with respect to each image for which the result of the additional external evaluation has been stored.

The system preferably comprises a processor and a memory that stores an evaluation software module, a request software module, and a transfer software module, wherein said evaluation unit is formed by the evaluation software module when the evaluation software module is executed by said processor, wherein said request unit is formed by the request software module when the request software module is executed by said processor, and wherein said transfer unit is formed by the transfer software module when the transfer software module is executed by said processor.

The system may also comprise at least one image acquisition unit configured to take images of patients' breasts and to forward the images to the evaluation unit.

Another exemplary embodiment of the present invention relates to a method of identifying breast cancer in at least one image of a patient's breast, the method comprising the following steps that are carried out by a computer:
analyzing the image,
generating a diagnosis result that labels the image as confident if the confidence in the evaluation result exceeds a given confidence level, and otherwise generates a diagnosis result that labels the image as unconfident,
generating an evaluation-request signal that requests an additional external evaluation of the image, if the diagnosis result labels the image as unconfident, and
blocking access to the diagnosis result until the result of the additional external evaluation has been received.

The above explanations with respect to systems and methods for identifying breast cancer can also be applied to other systems and methods that are directed to identifying other varieties of cancer.

Therefore, another exemplary embodiment of the present invention relates to a system for identifying cancer based on at least one image of a patient, the system comprising:
an evaluation unit configured to analyze the image, wherein the evaluation unit generates a diagnosis result that labels the image as confident if the confidence in the evaluation result exceeds a given confidence level, and otherwise generates a diagnosis result that labels the image as unconfident,
a request unit configured to generate an evaluation-request signal that requests an additional external evaluation of the image, if the diagnosis result labels the image as unconfident, and
a transfer unit having an input port for receiving the result of the additional external evaluation, and an output port for outputting the diagnosis result of the evaluation unit,
wherein the transfer unit is configured to block access to the diagnosis result of the evaluation unit until the result of the additional external evaluation has been received.

The above system for identifying cancer may have one or more features as defined in claims 2-18 of the present application as well as one or more of the features as shown in the figures and explained with reference to these figures.

Yet another exemplary embodiment of the present invention relates to a method of identifying cancer in at least one image of a patient, the method comprising the following steps that are carried out by a computer:
analyzing the image,
generating a diagnosis result that labels the image as confident if the confidence in the evaluation result exceeds a given confidence level, and otherwise generates a diagnosis result that labels the image as unconfident,
generating an evaluation-request signal that requests an additional external evaluation of the image, if the diagnosis result labels the image as unconfident, and
blocking access to the diagnosis result until the result of the additional external evaluation has been received.

The above method for identifying cancer may have one or more features as defined in claims 2-18 of the present application as well as one or more of the features as shown in the figures and explained with reference to these figures.

BRIEF DESCRIPTION OF THE DRAWINGS

In order that the manner in which the above-recited and other advantages of the invention are obtained will be readily understood, a more particular description of the invention briefly described above will be rendered by reference to specific embodiments thereof which are illustrated in the appended drawings. Understanding that these drawings depict only typical embodiments of the invention and are therefore not to be considered to be limiting of its scope, the invention will be described and explained with additional specificity and detail by the use of the accompanying drawings in which.

DETAILED DESCRIPTION OF THE PREFERRED EMBODIMENTS

The preferred embodiments of the present invention will be best understood by reference to the drawings. It will be readily understood that the present invention, as generally described and illustrated in the figures herein, could vary in a wide range. Thus, the following more detailed description of the exemplary embodiments of the present invention, as represented in the figures, is not intended to limit the scope of the invention, as claimed, but is merely representative of presently preferred embodiments of the invention.

Figure 1:
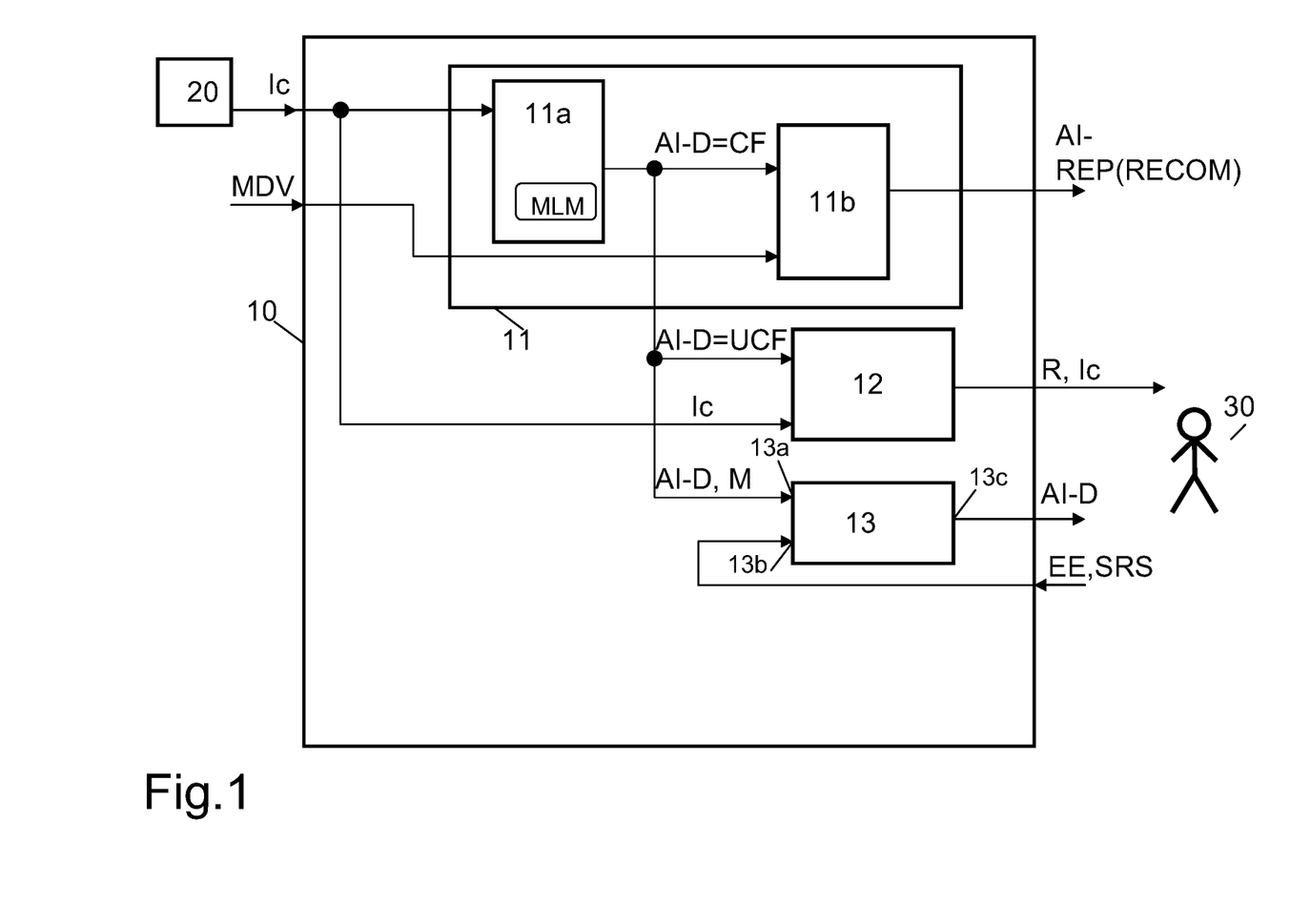
FIG. 1 illustrates a first exemplary embodiment of a system for identifying breast cancer, wherein the system of FIG. 1 evaluates current images of a patient's breast.

FIG. 1 depicts a first exemplary embodiment of a system 10 for identifying breast cancer on the basis of one or more images of a patient's breast. The term "patient" refers to human beings as well as animals regardless of their current health status and regardless of whether they are under medical treatment or not.

The system 10 of FIG. 1 comprises an evaluation unit 11, a request unit 12 and a transfer unit 13.

The evaluation unit 11 is configured to evaluate current images Ic that are taken by an image acquisition unit 20 such as for instance a camera, an x-ray transmission device, an ultrasonography device, a CT (computed tomography) device, a MRI (Magnetic resonance imaging) device, Tomosynthesis (3D images) device and the like. The image acquisition unit 20 may be an external device as shown in FIG. 1.

Alternatively, the image acquisition unit 20 may be an integral component of the system 10 itself. The latter case is depicted as a second exemplary embodiment in FIG. 2.

The evaluation of the current images Ic is based on artificial intelligence that is incorporated in an artificial intelligence subunit 11a. In prior training steps, the evaluation unit 11 and its artificial intelligence subunit 11a have been trained to identify cancer or cancer-suspicious areas in prior breast images of other patients. To this end, the artificial intelligence subunit 11a may comprise a machine learned model MLM. The machine learned model MLM may be based on or comprise a neural network, a Gaussian process, and/or a Bayesian model. For example, the artificial intelligence subunit 11a may comprise a deep convolutional network or a transformer based architecture that has been subjected to one or more prior training procedures to obtain the ability to analyze current breast images Ic with a given reliability.

After completion of each evaluation step, the artificial intelligence subunit 11a generates a diagnosis result AI-D that labels the current images Ic as confident "CF" if the confidence in the result exceeds a given confidence level. If the confidence in the result is below said given confidence level, the evaluation unit 11 generates a diagnosis result AI-D that labels the images Ic as unconfident "UCF".

If the evaluation unit 11 labels the current images Ic as unconfident "UCF", the request unit 12 generates an evaluation-request signal R that requests an additional external evaluation of the current images Ic. The external evaluation may be carried out by another technical system, for instance another artificial intelligence system, or a human being, preferably a doctor 30.

Figure 2:
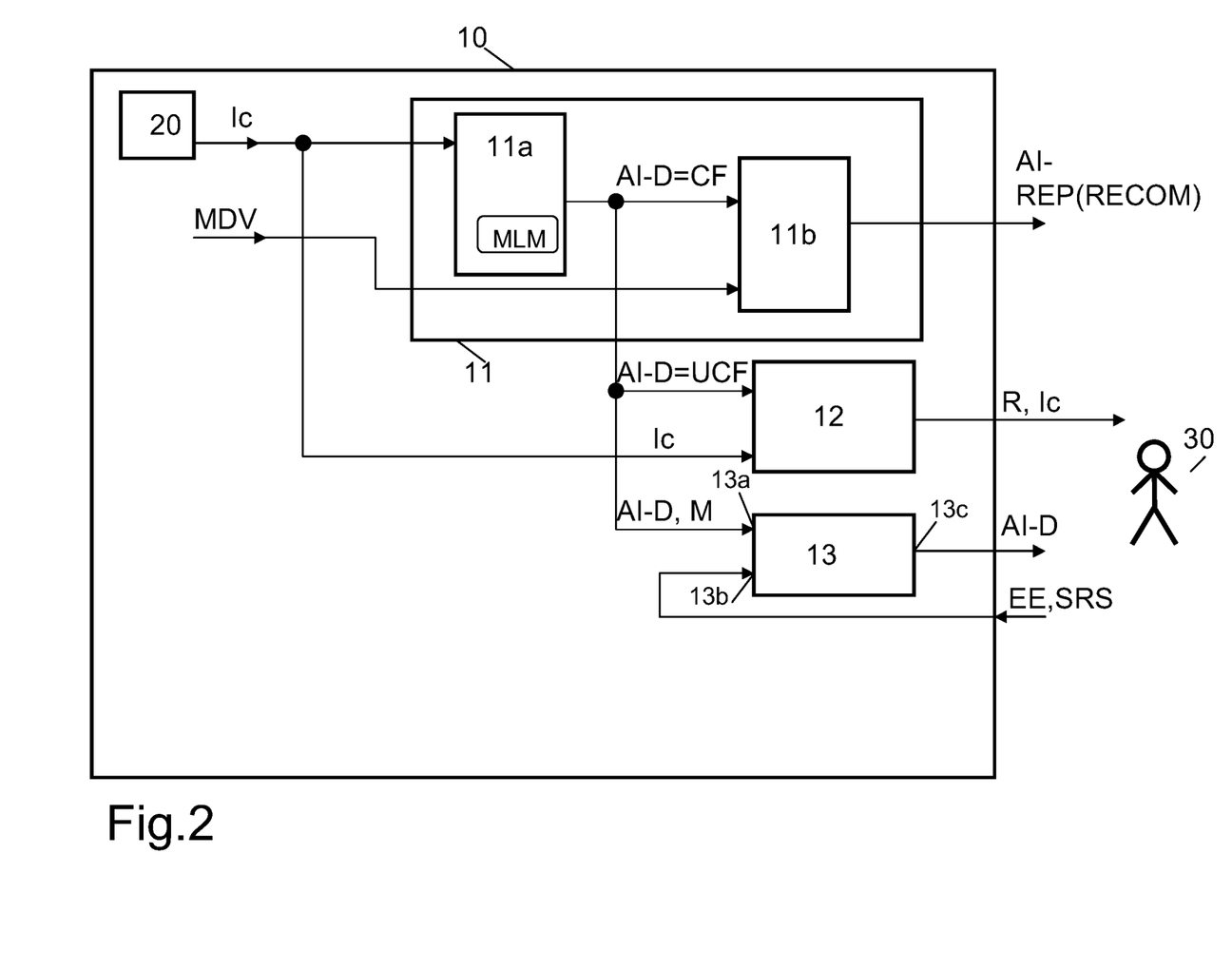
FIG. 2 illustrates a second exemplary embodiment of a system for identifying breast cancer on the basis of current images of a patient's breast, wherein the system of FIG. 2 additionally includes an image acquisition unit.

In the exemplary embodiment of FIGS. 1 and 2, the transfer unit 13 comprises a first input port 13a for receiving the diagnosis result AI-D of the artificial intelligence subunit 11a, and a second input port 13b for receiving the diagnosis result of the requested external evaluation EE.

An output port 13c of the transfer unit 13 is capable of outputting the diagnosis result AI-D of the evaluation unit 11, however, the outputting is delayed until the result of the external evaluation EE has been received at the second input port 13b. In other words, the transfer unit 13 blocks access to the diagnosis result AI-D of the evaluation unit 11 until the result of the external evaluation EE has been completed and entered into the system 10.

In the exemplary embodiment of FIGS. 1 and 2, the evaluation unit 11 further comprises a fully automated report unit 11b. If the evaluation unit 11 labels the current images Ic as confident, the report unit 11b automatically generates a medical report AI-REP that describes the diagnosis result AI-D, i.e. the fact that cancer has been detected or has not been detected, in a human readable or electronically readable format.

In the exemplary embodiment of FIGS. 1 and 2, the report unit 11b further evaluates a metadata vector MDV, if such a metadata vector MDV is provided at an input port of the evaluation unit 11.

Figure 2A:
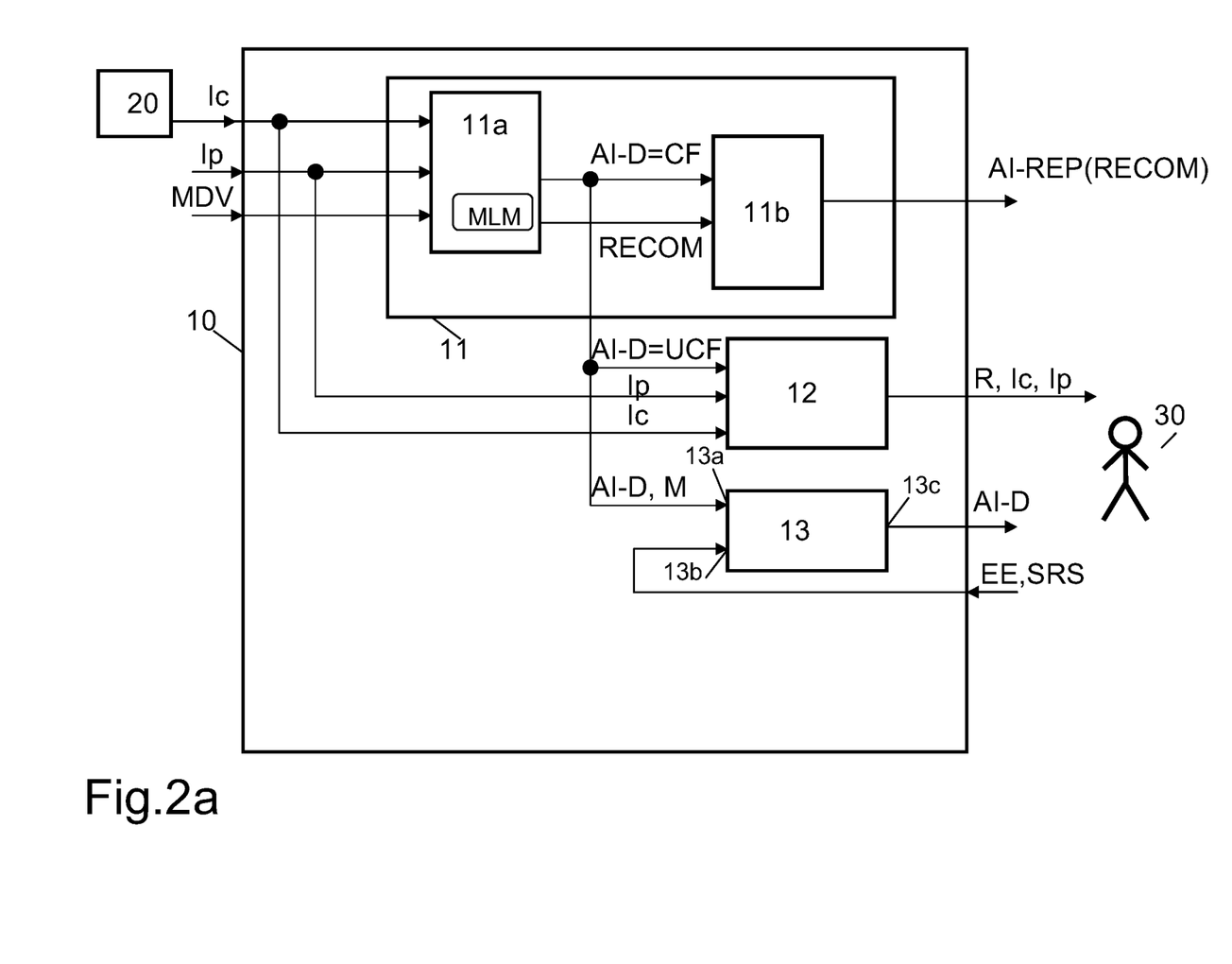
FIG. 2a illustrates a second exemplary embodiment of a system for identifying breast cancer on the basis of current images of a patient's breast, wherein the recommendation RECOM may be generated by the evaluation unit and transmitted to the report unit.

The metadata vector MDV comprises cancer-risk-relevant data of the current patient such that the medical report AI-REP may be more personalized. For instance, the report unit 11b may add a recommendation RECOM regarding time of a next screening and/or the modality of the next screening, to the medical report AI-REP based on the evaluation of the metadata vector MDV. Alternatively, the recommendation RECOM may be generated by the evaluation unit 11 and transmitted to the report unit 11b as shown in FIG. 2a.

The vector components of the metadata vector MDV may specify one or more of the following criteria: the number of cancers in the patient's first degree family, the number of breast cancers in the patient's first degree family, the number of cancers in the patient's second degree family, the number of breast cancers in the patient's second degree family, the patient's age, time since prior cancer diagnosis, genetic information, mutations in the BRCA1 gene, mutations in the BRCA2 gene, existence and type of palpable lesions.

For instance, the date of a recommended next screening may depend on the patient's age. E.g., the medical report AI-REP may schedule a recommended next screening sooner for younger patients and later for older patients.

Furthermore, the medical report AI-REP may schedule a recommended next screening rather sooner than later if mutations in the BRCA1 gene, mutations in the BRCA2 gene, and/or palpable lesions are indicated in the metadata vector MDV.

The artificial intelligence subunit 11a may be configured to add markings M to the current images Ic if unclear sections are detected. These markings M may be generated for instance by surrounding unclear sections and/or highlighting unclear sections and/or modifying colours of unclear sections. The markings M may be forwarded together with the diagnosis result AI-D or as a part thereof.

If markings M are available, the transfer unit 13 may output the added markings M upon receipt of the result of the external evaluation EE.

Additionally, the transfer unit 13 may be configured to output the markings M upon reception of an external support-request signal SRS at its second input port 13b. If for instance, a doctor 30 is not sure about her/his own diagnosis or cannot identify certain sections as cancer-free or cancer-affected, the doctor 30 may request and manually trigger the delivery of the diagnosis result AI-D of the artificial intelligence subunit 11a and/or the markings M before providing an own opinion.

Figure 3:
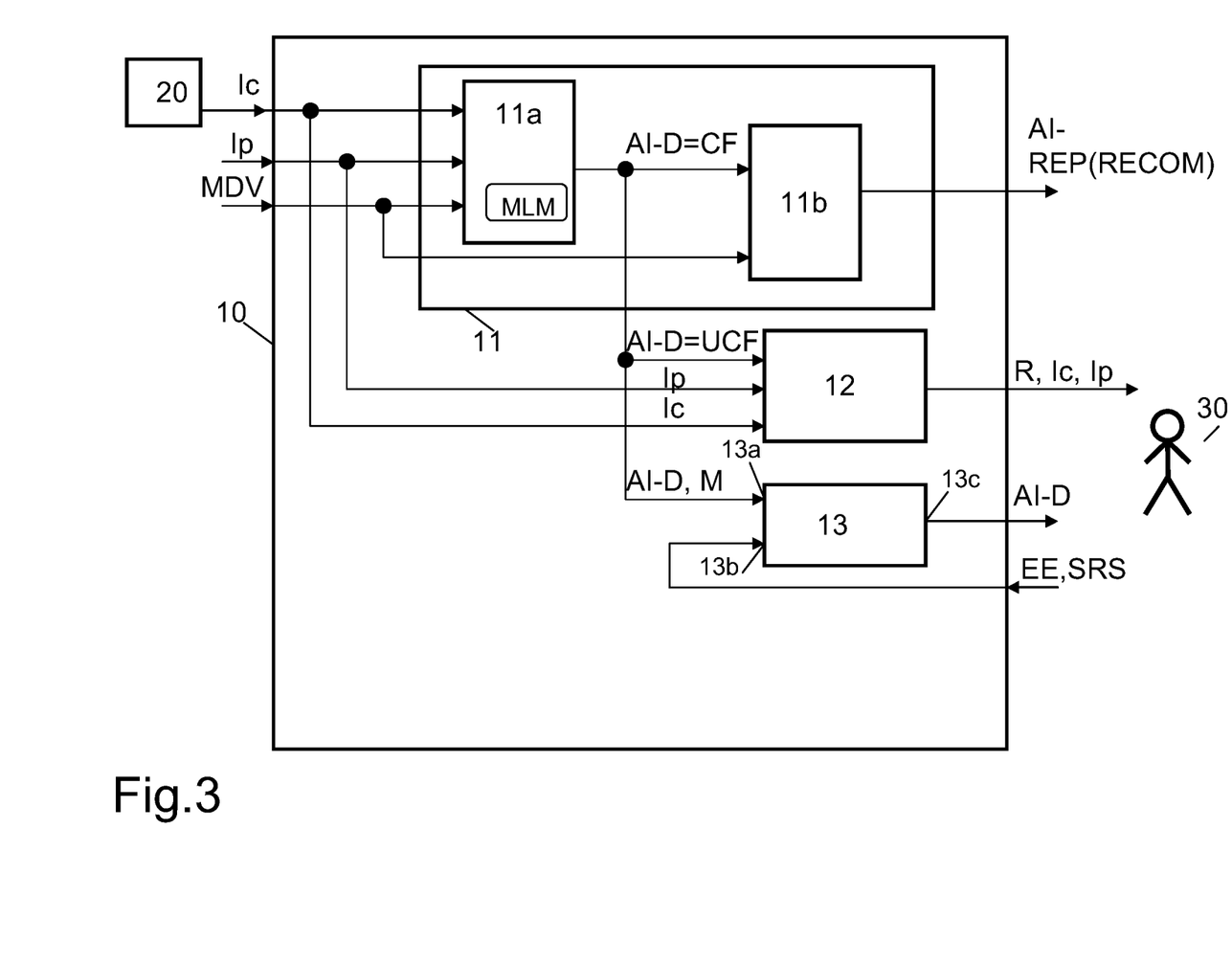
FIG. 3 illustrates a third exemplary embodiment of a system for identifying breast cancer, wherein the system of FIG. 3 evaluates current and previous images of a patient's breast.

FIG. 3 depicts a third exemplary embodiment of a system 10 for identifying breast cancer based on one or more current images Ic of a patient's breast.

The evaluation unit 11 in FIG. 3 comprises an artificial intelligence subunit 11a that is trained to additionally evaluate one or more prior breast images Ip of the same patient. The artificial intelligence subunit 11a of FIG. 3 may be also trained to include the metadata vector MDV mentioned above or at least one or more of its vector components into the evaluation process.

The prior breast images Ip have been taken during one or more evaluations prior to a current evaluation. The prior breast images Ip may be stored in an internal storage of the system 10 or an external storage. The artificial intelligence subunit 11a may request the delivery of internally or externally stored images Ip from the internal or external storage upon receipt of the current images Ic of the patient and/or the corresponding metadata vector MDV.

The additional evaluation of the prior breast images Ip preferably includes comparing the current breast images Ic with the prior breast images Ip. For instance, the development of the breast over time may be taken into account. E.g., the development of a certain spot over time, for instance from the year 2016 to the year 2018, from the year 2018 to the year 2020, and from the year 2020 to the year 2022, may be included in the generation of the diagnosis result AI-D.

Figure 4:
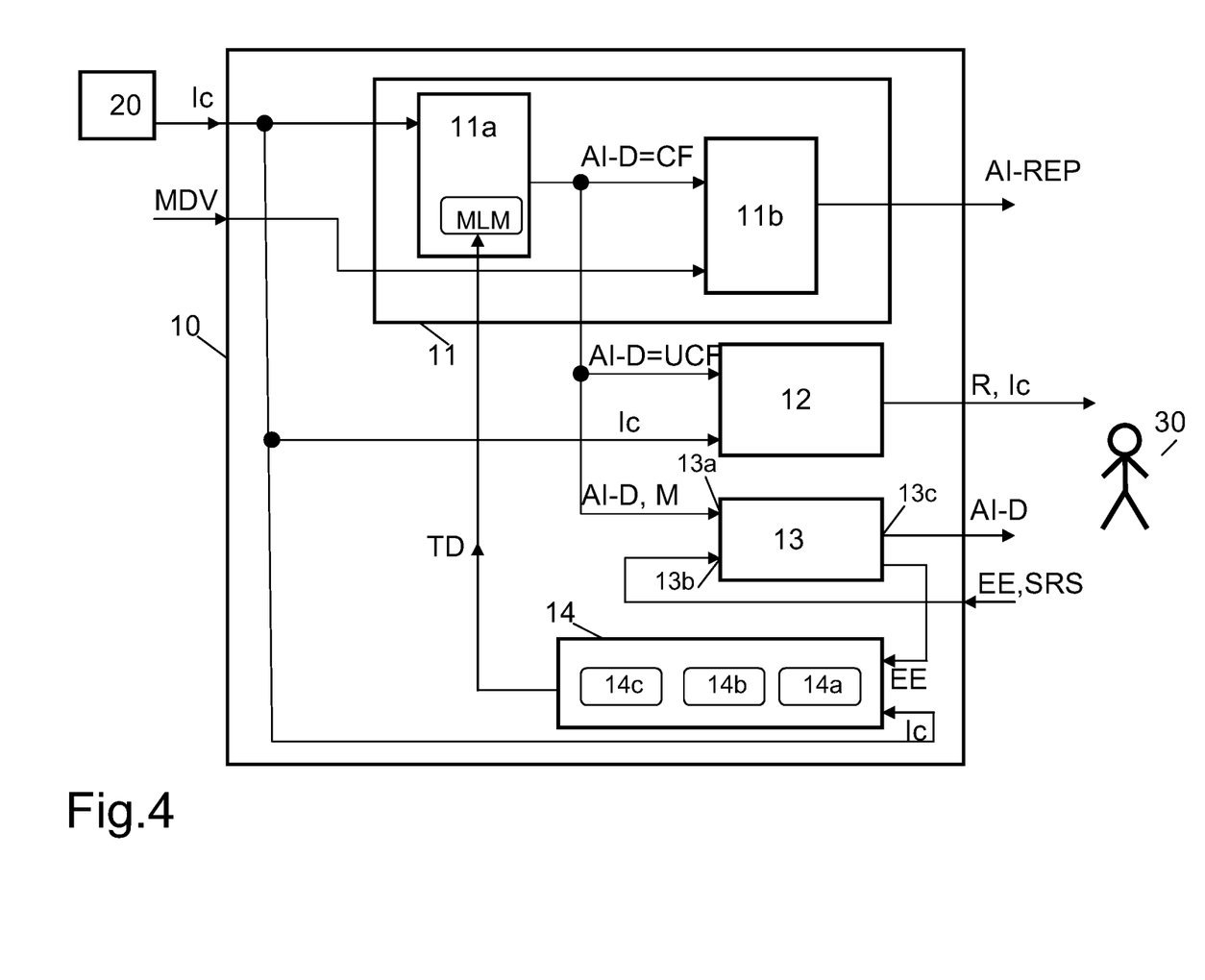
FIG. 4 illustrates a fourth exemplary embodiment of a system for identifying breast cancer, wherein the system of FIG. 4 evaluates current images of a patient's breast and includes a training unit.

FIG. 4 depicts a fourth exemplary embodiment of a system 10 for identifying breast cancer based on one or more current images Ic of a patient's breast.

The system 10 of FIG. 4 is similar to the embodiment of FIGS. 1 and 2. The only difference is an additional integrated training unit 14 that is configured to train the machine learned model MLM of the artificial intelligence subunit 11a.

To this end, the integrated training unit 14 of FIG. 4 comprises an internal storage 14a for storing the results of the external evaluations EE for use in later training sessions. The results of the external evaluations EE may be provided by the transfer unit 13 upon receipt of such external results.

The training unit 14 is configured to generate training data TD on the basis of the results of the external evaluations EE and the corresponding images Ic. The training unit 14 is further capable of training the machine learned model MLM on the basis of the generated training data TD.

The training unit 14 may be based on artificial intelligence that is incorporated inside an artificial intelligence subunit 14b of the training unit 14. In prior training steps, the artificial intelligence subunit 14b of the training unit 14 may have been trained to generate said training data TD on the basis of prior images Ic, corresponding results of prior external evaluations EE and corresponding prior training data. The artificial intelligence subunit 14b may comprise a machine learned model, for instance a neural network, a Gaussian process, and/or a Bayesian model.

The training unit 14 may be configured to carry out an individual training session with respect to each image Ic for which the result of the external evaluation EE has been stored. Alternatively, the training unit 14 may comprise an internal trigger unit 14c that counts the number of stored external evaluations EE and/or measures the time that has passed since the last training session.

The trigger unit 14c may trigger a training session when the number of stored external evaluations EE exceeds a given number and/or the time that has passed since the last training session exceeds a given threshold.

Figure 5:
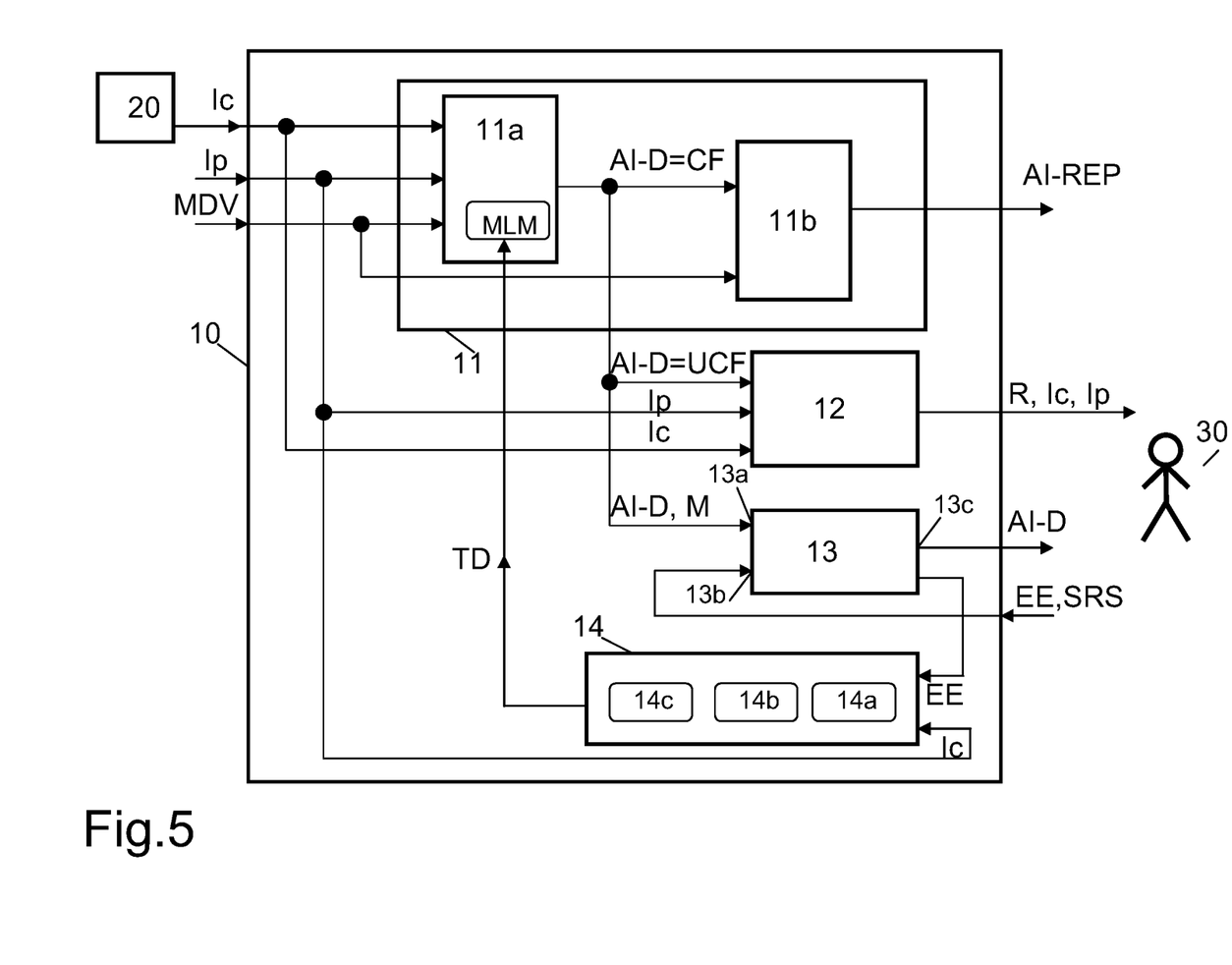
FIG. 5 illustrates a fifth exemplary embodiment of a system for identifying breast cancer, wherein the system of FIG. 5 evaluates current and previous images of a patient's breast and includes a training unit.

FIG. 5 depicts a fifth exemplary embodiment of a system 10 for identifying breast cancer based on one or more current images Ic of a patient's breast.

The system 10 of FIG. 5 is similar to the embodiment of FIG. 3. The only difference is the additional integrated training unit 14 that may be identical to the training unit 14 of FIG. 4.

Figure 6:
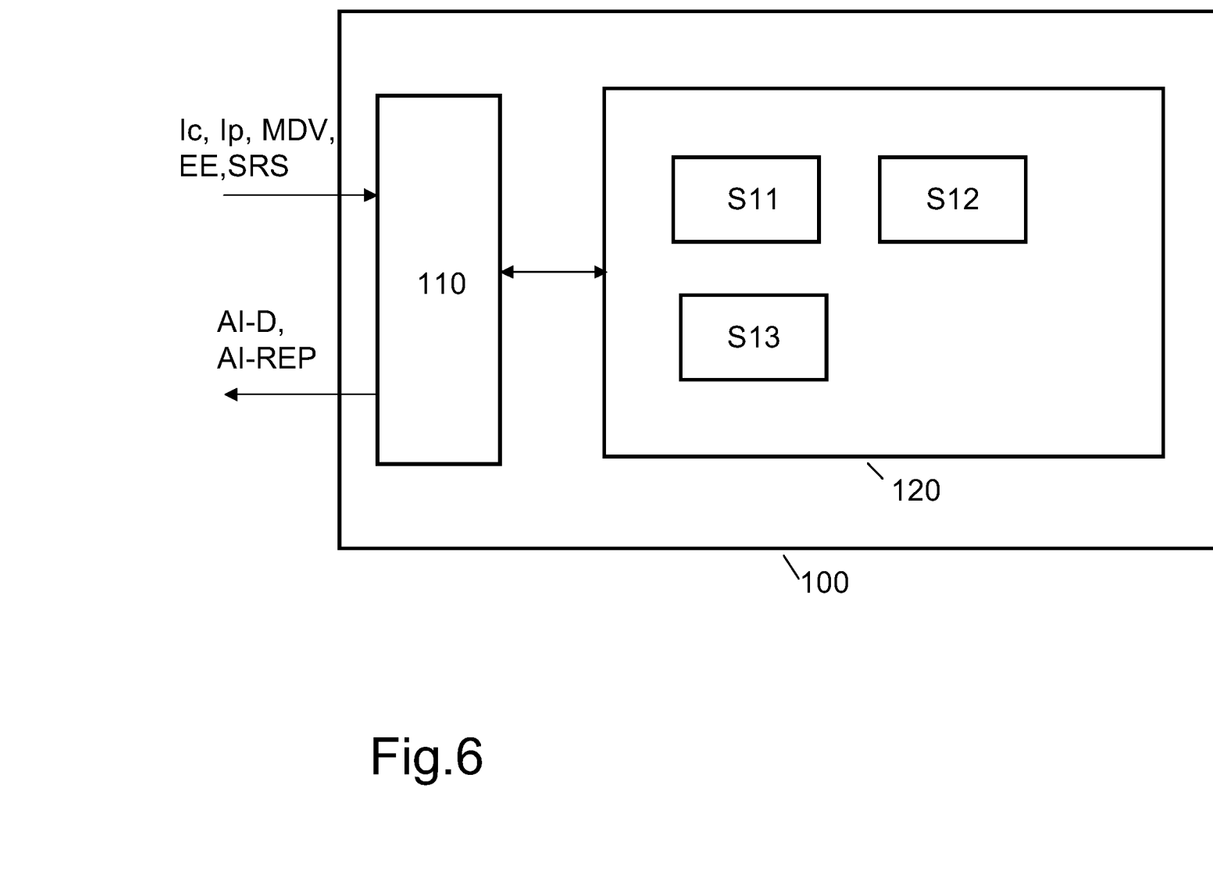
FIG. 6 illustrates an exemplary embodiment of a computer system that may be part of the systems shown in FIGS. 1-5 or even form the systems of FIGS. 1-3.

FIG. 6 depicts an exemplary embodiment of a computer system 100 that may be part of the systems 10 shown in FIGS. 1-5 or even form the systems 10 of FIGS. 1-3. The computer system 100 of FIG. 6 comprises a processor 110 and a memory 120. The memory 120 stores an evaluation software module S11, a request software module S12, and a transfer software module S13.

The evaluation software module S11 forms or acts as the evaluation unit 11 of FIGS. 1-5 when executed by the processor 110. The request software module S12 forms or acts as the request unit 12 of FIGS. 1-5 when executed by the processor 110. The transfer software module S13 forms or acts as the transfer unit 13 of FIGS. 1-5 when executed by the processor 110.

Figure 7:
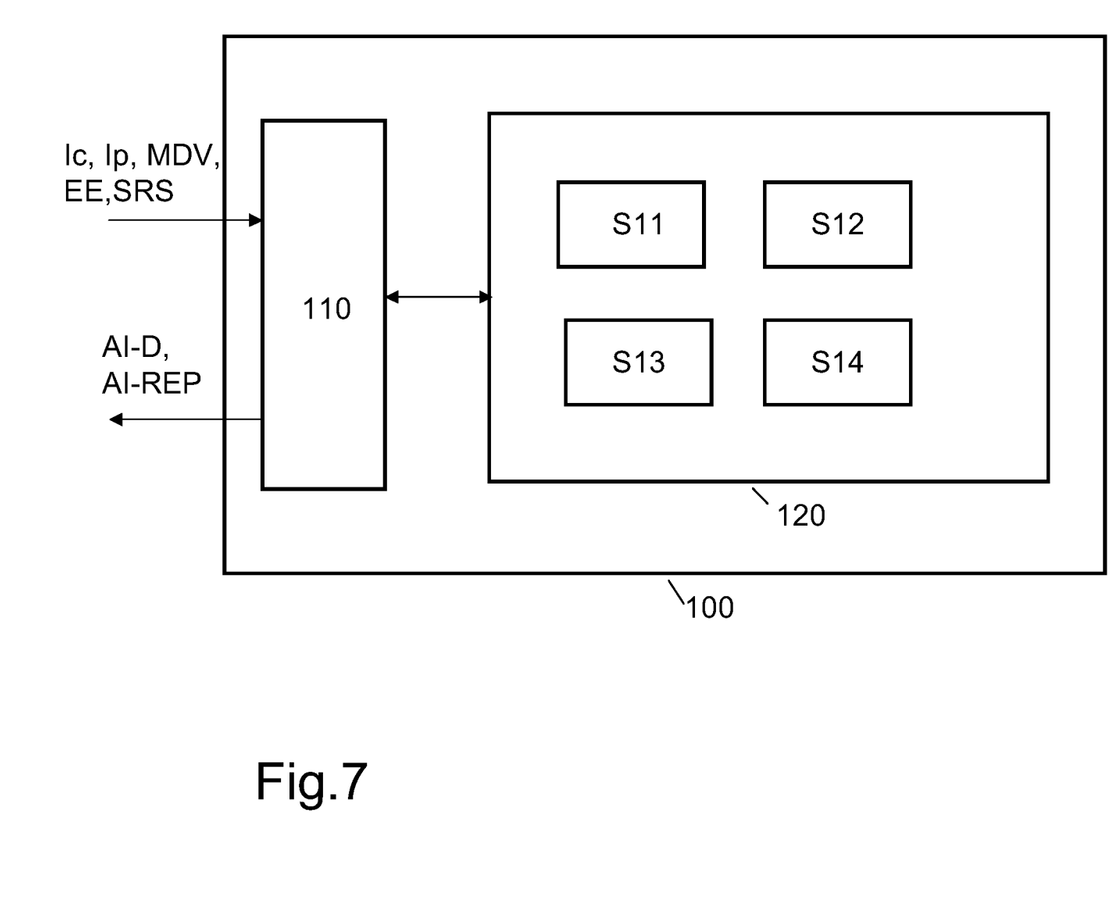
FIG. 7 illustrates an exemplary embodiment of a computer system that may be part of the systems shown in FIGS. 1-5 or even form said systems.

FIG. 7 depicts a second exemplary embodiment of a computer system 100 that may be part of the systems 10 shown in FIGS. 1-5 or even form the systems 10 of FIGS. 1-3. The computer system 10 of FIG. 7 is similar to the computer system 10 of FIG. 6 and only differs in an additional training software module S14.

The training software module forms or acts as the training module 14 of FIGS. 4 and 5 when executed by the processor 110.

The various embodiments and aspects of embodiments of the invention disclosed herein are to be understood not only in the order and context specifically described in this specification, but to include any order and any combination thereof. Whenever the context requires, all words used in the singular number shall be deemed to include the plural and vice versa. Whenever the context requires, all options that are listed with the word "and" shall be deemed to include the world "or" and vice versa, and any combination thereof.

In the drawings and specification, there have been disclosed a plurality of embodiments of the present invention. The applicant would like to emphasize that each feature of each embodiment may be combined with or added to any other of the embodiments in order to modify the respective embodiment and create additional embodiments. These additional embodiments form a part of the present disclosure and, therefore, the applicant may file further patent claims regarding these additional embodiments at a later stage of the prosecution.

Further, the applicant would like to emphasize that each feature of each of the following dependent claims may be combined with any of the present independent claims as well as with any other (one or more) of the present dependent claims (regardless of the present claim structure). Therefore, the applicant may direct further patent claims towards other claim combinations at a later stage of the prosecution.

For instance, the method claim 19 may comprise features mentioned in any of the claims 1-18 (and in any combination).

The invention claimed is:

1. System for identifying breast cancer based on at least one image of a patient's breast, the system comprising:
an evaluation unit configured to analyze the image, wherein the evaluation unit generates a diagnosis result that labels the image as confident if the confidence in the evaluation result exceeds a given confidence level, and otherwise generates a diagnosis result that labels the image as unconfident,
wherein the evaluation unit comprises a machine learned model,
a request unit configured to generate an evaluation-request signal that requests an additional external evaluation of the image, if the diagnosis result labels the image as unconfident, and
a transfer unit having an input port for receiving the result of the additional external evaluation, and an output port for outputting the diagnosis result of the evaluation unit,
wherein the transfer unit is configured to block access to the diagnosis result of the evaluation unit until the result of the additional external evaluation has been received,
an integrated training unit configured to train the machine learned model,
wherein the system stores available results of external evaluations for use in a later training session,
wherein said transfer unit is configured to transfer the results of the additional external evaluation towards the training unit, and
wherein the training unit is configured to generate training data on the basis of the results of the additional external evaluation and the corresponding image or images, and to train the machine learned model on the basis of the generated training data, and
wherein the system generates a trigger signal in order to trigger a training session when the number of stored external evaluations exceeds a given number and/or the time that has passed since the last training session exceeds a given threshold.

2. System of claim 1 wherein the transfer unit is configured to output the diagnosis result of the evaluation unit at the output port upon receipt of the result of the additional external evaluation.

3. System of claim 1
wherein the evaluation unit is configured to further evaluate a metadata vector that comprises cancer-risk-relevant data of the patient, and
wherein the further evaluation of the metadata vector includes generating the diagnosis result based on the metadata vector in order to generate a vector-based diagnosis result.

4. System of claim 1 wherein the evaluation unit generates a medical report if the diagnosis result labels the image as confident.

5. System of claim 4
wherein the evaluation unit is configured to further evaluate a metadata vector that comprises cancer-risk-relevant data of the patient, and
wherein the further evaluation of the metadata vector includes generating the medical report based on the metadata vector in order to generate a vector-based medical report.

6. System of claim 5 wherein the evaluation unit is configured to add a recommendation regarding time of a next screening and/or the modality of the next screening, to the vector-based medical report based on the evaluation of the metadata vector.

7. System of claim 6 wherein vector components of the metadata vector specify one or more of the following criteria:
the number of cancers in the patient's first degree family,
the number of breast cancers in the patient's first degree family,
the number of cancers in the patient's second degree family,
the number of breast cancers in the patient's second degree family,
the patient's age,
time since prior cancer diagnosis,
genetic information,
mutations in the BRCA1 gene,
mutations in the BRCA2 gene,
existence and type of palpable lesions.

8. System of claim 1
wherein the evaluation unit is configured to additionally evaluate one or more stored prior breast images of the same patient, said prior breast images being taken during one or more evaluations prior to a current evaluation,
wherein the additional evaluation of said one or more prior breast images includes comparing at least one stored prior breast image with at least one current breast image that is taken during said current evaluation, and
wherein the result of said comparison is included in the generation of the diagnosis result.

9. System of claim 1 wherein the evaluation unit is configured to generate markings that identify unclear sections of the image.

10. System of claim 9 wherein the transfer unit outputs the markings upon receipt of the result of the additional external evaluation or upon receipt of an external support-request signal at the input port.

11. System for identifying breast cancer based on at least one image of a patient's breast, the system comprising:
an evaluation unit configured to analyze the image, wherein the evaluation unit generates a diagnosis result that labels the image as confident if the confidence in the evaluation result exceeds a given confidence level, and otherwise generates a diagnosis result that labels the image as unconfident,
wherein the evaluation unit comprises a machine learned model,
a request unit configured to generate an evaluation-request signal that requests an additional external evaluation of the image, if the diagnosis result labels the image as unconfident, and
a transfer unit having an input port for receiving the result of the additional external evaluation, and an output port for outputting the diagnosis result of the evaluation unit,
wherein the transfer unit is configured to block access to the diagnosis result of the evaluation unit until the result of the additional external evaluation has been received,
an integrated training unit configured to train the machine learned model,
wherein the system stores available results of external evaluations for use in a later training session, wherein said transfer unit is configured to transfer the results of the additional external evaluation towards the training unit, and wherein the training unit is configured to generate training data on the basis of the results of the additional external evaluation and the corresponding image or images, and to train the machine learned model on the basis of the generated training data, and wherein the training unit is configured to carry out an individual training session with respect to each image for which the result of the additional external evaluation has been stored.

12. System of claim 1, wherein the system comprises a processor and a memory that stores an evaluation software module, a request software module, and a transfer software module, wherein said evaluation unit is formed by the evaluation software module when the evaluation software module is executed by said processor, wherein said request unit is formed by the request software module when the request software module is executed by said processor, and wherein said transfer unit is formed by the transfer software module when the transfer software module is executed by said processor.

13. System of claim 12, wherein the system comprises at least one image acquisition unit configured to take images of patients' breasts and to forward the images to the evaluation unit.

14. Method of identifying breast cancer in at least one image of a patient's breast, the method comprising the following steps that are carried out by a computer:

analyzing the image using an evaluation, wherein the evaluation unit comprises a machine learned model, generating a diagnosis result using the evaluation unit, wherein the diagnosis result labels the image as confident if the confidence in the evaluation result exceeds a given confidence level, and otherwise generates a diagnosis result that labels the image as unconfident, generating an evaluation-request signal using a request unit, wherein the signal requests an additional external evaluation of the image if the diagnosis result labels the image as unconfident, providing a transfer unit having an input port for receiving the result of the additional external evaluation, and an output port for outputting the diagnosis result of the evaluation unit, and blocking access to the diagnosis result using the transfer unit until the result of the additional external evaluation has been received, providing an integrated training unit configured to train the machine learned model, storing available results of external evaluations for use in a later training session, transferring the results of the additional external evaluation towards the training unit using the transfer unit, and generating training data, using the training unit, on the basis of the results of the additional external evaluation and the corresponding image or images, and training the machine learned model on the basis of the generated training data, and carrying out individual training sessions, using the training unit, with respect to each image for which the result of the additional external evaluation has been stored.

15. Method of identifying breast cancer in at least one image of a patient's breast, the method comprising the following steps that are carried out by a computer:

analyzing the image using an evaluation, wherein the evaluation unit comprises a machine learned model, generating a diagnosis result using the evaluation unit, wherein the diagnosis result labels the image as confident if the confidence in the evaluation result exceeds a given confidence level, and otherwise generates a diagnosis result that labels the image as unconfident, generating an evaluation-request signal using a request unit, wherein the signal requests an additional external evaluation of the image if the diagnosis result labels the image as unconfident, providing a transfer unit having an input port for receiving the result of the additional external evaluation, and an output port for outputting the diagnosis result of the evaluation unit, and blocking access to the diagnosis result using the transfer unit until the result of the additional external evaluation has been received, providing an integrated training unit configured to train the machine learned model, storing available results of external evaluations for use in a later training session, transferring the results of the additional external evaluation towards the training unit using the transfer unit, and generating training data, using the training unit, on the basis of the results of the additional external evaluation and the corresponding image or images, and training the machine learned model on the basis of the generated training data, and generating a trigger signal in order to trigger a training session when the number of stored external evaluations exceeds a given number and/or the time that has passed since the last training session exceeds a given threshold.

16. System of claim 11 wherein the transfer unit is configured to output the diagnosis result of the evaluation unit at the output port upon receipt of the result of the additional external evaluation.

17. System of claim 11 wherein the evaluation unit is configured to further evaluate a metadata vector that comprises cancer-risk-relevant data of the patient, and wherein the further evaluation of the metadata vector includes generating the diagnosis result based on the metadata vector in order to generate a vector-based diagnosis result.

18. System of claim 11 wherein the evaluation unit generates a medical report if the diagnosis result labels the image as confident.

19. System of claim 11 wherein the evaluation unit is configured to additionally evaluate one or more stored prior breast images of the same patient, said prior breast images being taken during one or more evaluations prior to a current evaluation, wherein the additional evaluation of said one or more prior breast images includes comparing at least one stored prior breast image with at least one current breast image that is taken during said current evaluation, and wherein the result of said comparison is included in the generation of the diagnosis result.

20. System of claim 11 wherein the evaluation unit is configured to generate markings that identify unclear sections of the image.

21. System of claim 11,
wherein the system comprises a processor and a memory that stores an evaluation software module, a request software module, and a transfer software module,
wherein said evaluation unit is formed by the evaluation software module when the evaluation software module is executed by said processor,
wherein said request unit is formed by the request software module when the request software module is executed by said processor, and
wherein said transfer unit is formed by the transfer software module when the transfer software module is executed by said processor.

* * * * *